(12) United States Patent
Wilser et al.

(10) Patent No.: US 8,241,220 B2
(45) Date of Patent: Aug. 14, 2012

(54) BIPLANE ULTRASOUND IMAGING AND CORRESPONDING TRANSDUCER

(75) Inventors: Walter T. Wilser, Cupertino, CA (US); Lex Garbini, El Granada, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1232 days.

(21) Appl. No.: 11/805,162

(22) Filed: May 21, 2007

(65) Prior Publication Data
US 2008/0294052 A1    Nov. 27, 2008

(51) Int. Cl.
*A61B 8/00* (2006.01)

(52) U.S. Cl. .................... 600/466; 600/463

(58) Field of Classification Search .............. 600/466
See application file for complete search history.

(56) References Cited

U.S. PATENT DOCUMENTS

| | | | |
|---|---|---|---|
| 5,876,345 A | 3/1999 | Eaton et al. | |
| 6,014,473 A * | 1/2000 | Hossack et al. | 382/294 |
| 6,296,619 B1 * | 10/2001 | Brisken et al. | 604/22 |
| 6,915,696 B2 | 7/2005 | Dufait et al. | |

* cited by examiner

*Primary Examiner* — Jonathan Cwern (57) ABSTRACT

An ultrasonic imaging tube is provided. A tube body has a longitudinal axis and a circumference. A first transducer array is disposed in the body along the longitudinal axis. A second transducer array is disposed in the body along the longitudinal axis. The first transducer array is substantially parallel with the second transducer array. The first transducer array and the second transducer array are at a first non-zero angle to each other about the longitudinal axis.

18 Claims, 5 Drawing Sheets

BIPLANE ULTRASOUND IMAGING AND CORRESPONDING TRANSDUCER

BACKGROUND

The present invention relates to medical imaging. In particular, transducer arrays disposed within an inter-cavity, intra-operative, or catheter housing is provided.

Medical imaging involves several invasive and non-invasive techniques and procedures. Non-invasive imaging using ultrasound, magnetic resonance imaging ("MRI"), positron emission tomography ("PET"), and computed tomography ("CT"), commonly occurs everyday. Physicians, technicians, and medical professionals also utilize invasive imaging for diagnostic and treatment purposes. For example, in the field of endoscopy, doctors may use various scopes or tubes to view the inner anatomy and physiology of a patient, such as a human or animal. Furthermore, doctors, such as cardiologists, may use ultrasonic catheters to view internal anatomy, such as the inner chambers of a heart. Generally, ultrasonic catheters include a transducer array that is used to convert between electrical and acoustic energies for generating images of internal organs and physiology.

Known ultrasonic catheters may utilize one transducer array for scanning a two dimensional region while maneuvering the catheter within a body. A three dimensional ("3D") volume may be scanned by rotating the ultrasonic catheter back and forth to capture a plurality of data. In a transducer probe used outside the body of a patient, mechanical structures, commonly referred to as a "wobbler," rotate the array.

Biplane transducer arrays that are rotated 90 degrees from each other (i.e., a+or T shape) are used to allow a doctor to view two image planes at once. However, such a design may not fit in a catheter, especially due to the number of cable connections needed to communicate with the transducer arrays and the small size of catheters.

BRIEF SUMMARY

By way of introduction, the preferred embodiments described below include transducer arrays, imaging tubes, and methods of imaging. At least two transducer arrays are disposed in a tube body. The transducer arrays are substantially parallel to each other along the tube body and are at a non-zero angle to each other.

In a first aspect, an ultrasonic imaging tube is provided. A tube body has a longitudinal axis and a circumference. A first transducer array is disposed in the body along the longitudinal axis. A second transducer array is disposed in the body along the longitudinal axis. The first transducer array is substantially parallel with the second transducer array. The first transducer array and the second transducer array are at a first non-zero angle to each other about the longitudinal axis.

In a second aspect, an ultrasonic catheter is provided. A lumen of a catheter is operable to connect with an ultrasound machine. A first one dimensional linear phased transducer array is disposed in the lumen with a first azimuth axis that is substantially parallel with a longitudinal axis of the lumen. A second one dimensional linear phased transducer array is disposed in the lumen with a second azimuth axis that is substantially parallel with the longitudinal axis of the lumen. The first and second one dimensional linear phased transducer arrays are at a first non-zero angle to each other about the longitudinal axis.

In a third aspect, a method of imaging is provided. A tube is inserted into a patient. The tube has a longitudinal axis and a circumference. A first transducer array is disposed in the tube, and a second transducer array is disposed in the tube. The first transducer array and the second transducer array are at a first non-zero angle to each other about the longitudinal axis. The first transducer array is spaced apart from the second transducer array. A first image data is acquired in a first image plane aligned with the first transducer array. A second image data is acquired in a second image plane aligned with the second transducer array. The longitudinal axis is within each of the first and second image planes. The first image plane diverges from the second image plane at the first non-zero angle.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

An imaging tube, such as a catheter, has at least two transducer arrays disposed in a tube body. The at least two transducer arrays are both aligned with a longitudinal axis of the tube, but they are aimed to result in two 2D images at an angle to each other. Such a design is easy to manufacture. Also, this gives a doctor or other medical professional at least two simultaneous views of an internal anatomical structure, such as a heart, of a patient. By watching the two images associated with different planes, the doctor can get an idea of the anatomy and the 3D landscape. In addition, the image data can be used to generate a 3D volume image.

Figure 1:
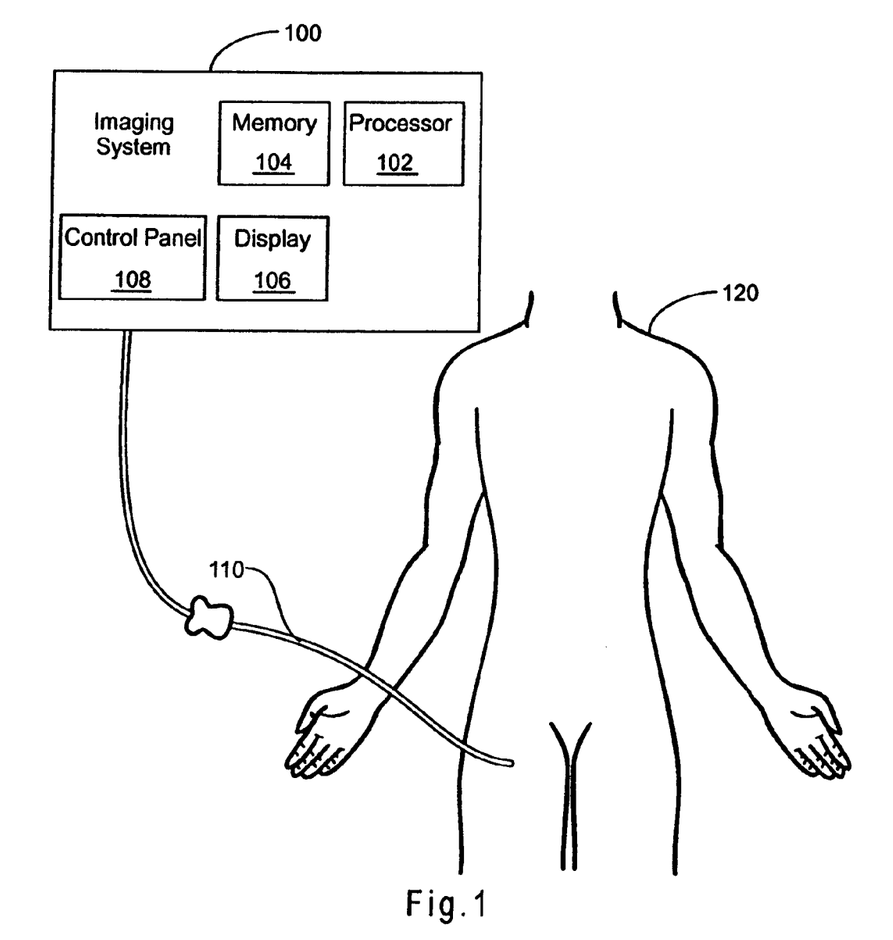
FIG. 1 is a general diagram illustrating one embodiment of an imaging tube.

FIG. 1 is a general diagram illustrating one embodiment of an imaging tube 110. The imaging tube 110 is operable to connect to an imaging system 100. The imaging tube is also operable to be inserted into a patient 120.

The imaging system 100 is an ultrasound system, an endoscopy system, or any known or future medical imaging system. For example, the imaging system 100 is a medical diagnostic imaging system with transmit and receive beamformers, one or more detectors (e.g., B-mode and/or Doppler), and a scan converter. The imaging system 100 includes a processor 102, memory 104, display 106, control panel and control keys 108, or any known or future electronic and/or audio/visual hardware used for medical imaging.

The processor 102 is in communication with the memory 104, the display 106, and the control panel 108. The processor 102 is a main processor, such as a microprocessor, or a plurality of processors operable to communicate with electronics of the imaging system 100. The memory 104 is any known or future storage device. The memory 104 is a non-volatile and/or volatile memory, such as a Random Access Memory "RAM" (electronic), a Read-Only Memory "ROM" (electronic), or an Erasable Programmable Read-Only Memory (EPROM or Flash memory). The display 106 is any mechanical and/or electronic display positioned for accessible viewing by a doctor or medical professional. For example, the display 106 is a liquid crystal display, ("LCD") or CRT monitor. The display 106 is operable to show 2D, 3D, and/or four dimensional ("4D") images (i.e., the fourth dimension is identified with time, and, therefore, 4D images are images that show an object over a time period). The control panel 108 includes, but is not limited to, buttons or any other input device for sending commands.

The imaging system 100 is operable to process or run any variety of known of future medical imaging software protocols and/or applications. For example, the imaging system 100 includes or is operable to load programs or applications for processing ultrasonic image data and rendering 2D, 3D, and/or 4D images, in which the images are displayed by the imaging system 100 for diagnostic, research, and/or treatment purposes.

The patient 120 is any living or nonliving object. For example, the patient 120 is an animal or human being. The imaging tube 110 is inserted through any part or region of the patient 120 to image any anatomical or physiological feature of the patient 120. For example, to image portions of a heart of the patient 120, the imaging tube is inserted into a limb, such as an arm or leg, of the patient 120 to enter into a vein or artery that leads to the heart. For example, the imaging tube 110 is inserted into a femoral vein of the patient 120. Alternatively, other organs or internal regions of the patient 120 are imaged by inserting the imaging tube 110 in the throat, chest, abdomen, any opening or orifice, or any other part of the patient 120.

The imaging tube 110 is an imaging catheter, an ultrasonic catheter, an endoscope, or any other flexible or rigid tube that is used for imaging internal features, anatomy, or functions of an object, such as the patient 120. For example, the imaging tube 110 is an ultrasonic catheter or endoscope utilizing transducers to generate images via sound waves. The imaging tube 110 includes a body or lumen having a longitudinal axis and a circumference. The body or lumen is a flexible shaft that is made of a plastic, a polymer, and/or any known or future flexible material. For example, the body is made of Pebax, manufactured by ELF ATOCHEM North America, Inc. of Philadelphia, Pa. The body or lumen of the imaging tube 110 has a length ranging from about 60 cm to about 120 cm and an outer diameter ranging from about 1 mm to about 4 mm. However, any length and inner or outer diameter may be used. Also, the imaging tube 110 may include a handle and/or a steering mechanism.

The imaging tube 110, such as an ultrasonic catheter, may be designed to have carved out slots or grooves for disposing transducer arrays at various angles and positions. For example, any number of transducer arrays may be set in predetermined slots in the imaging tube 110, and then the imaging tube may be exposed to a certain temperature that melts the imaging tube 110, without deforming the basic structure of the tube, to bond the transducer arrays to the inner surface of the body. This allows the transducer arrays to be positioned at various angles to each other.

Figures 2, 3:
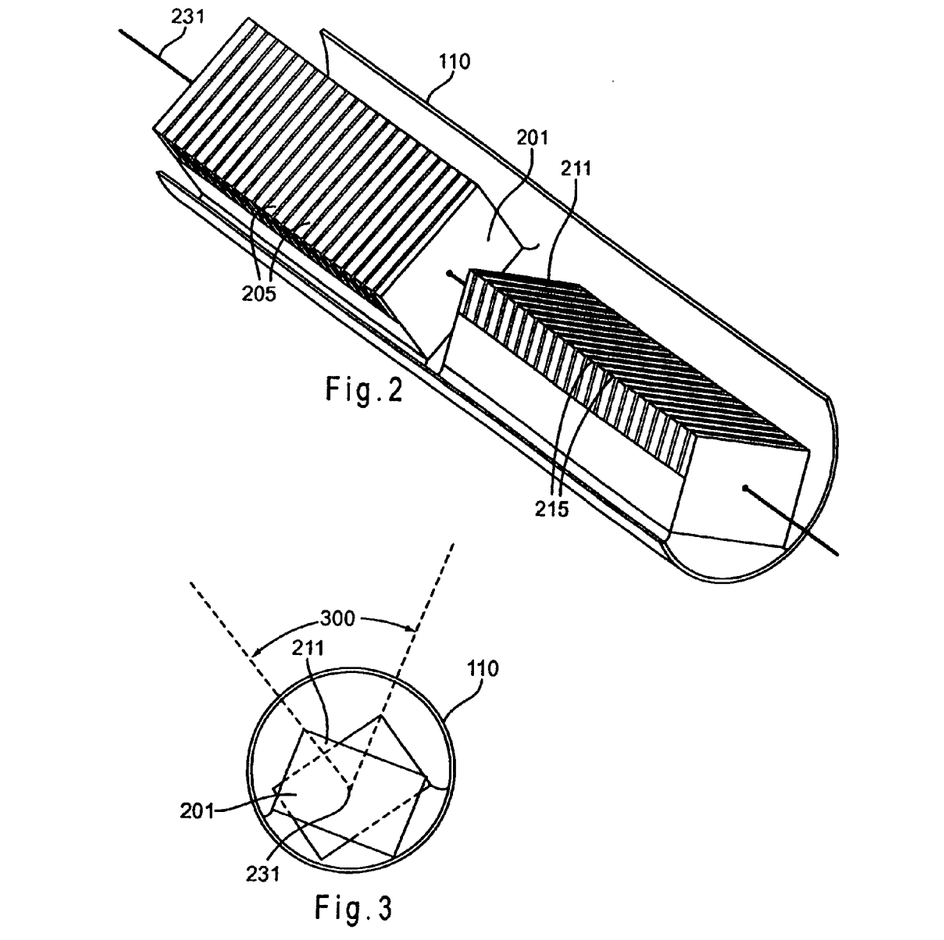
FIG. 2 is a magnified view of one embodiment of the imaging tube of FIG. 1.
FIG. 3 is a front view of the imaging tube of FIG. 2.

FIG. 2 shows a magnified view of one embodiment of the imaging tube 110 of FIG. 1. Transducer arrays 201 and 211 are disposed in the body of the imaging tube 110 along the longitudinal axis 231. The transducer arrays 201 and 211 are any known or future type of transducer array. For example, the transducer arrays 201 and 211 are one dimensional linear phased transducer arrays. Each of the transducer arrays 201 and 211 has a plurality of elements, 205 and 215, respectively. For example, the elements 205 and 215 are about 64 in number for the transducer arrays 201 and 211, respectively. However, any number of transducer elements for each array may be used.

The transducer elements 205 or 215 are formed from transducer material. The transducer material is piezoelectric ("PZT"), ceramic, silicon, semiconductor and/or membrane, but other materials or structures may be used to convert between acoustical and electrical energies. Alternatively, the transducer material is a multi-layered transducer material having at least two layers of transducer material. Multiple layers of transducer material may be bonded together via sintering, lamination, asperity contact, or any other chemical or mechanical structure or technique used to hold the layers together. Also, the multiple layers of transducer material are electrically interconnected by vias, electrode arrangements, such as signal and ground electrodes with or without discontinuities on each layer of transducer material, traces, TAB like jumpers, wire bonding, and/or any other electrical interconnection.

Alternatively, the transducer material is a semiconductor substrate with one or more flexible membranes (e.g., tens or hundreds for each element) formed within or on the semiconductor substrate. The flexible membrane has an electrode on at least one surface for transducing between energies using a capacitive effect, such as provided in capacitive membrane ultrasound transducers. The membrane is formed with silicon or other materials deposited or formed on the semiconductor substrate.

The transducer elements 205 or 215 may also include any number of different layers, such as matching layers, flex circuit layers, signal traces, electrodes, a lens and/or a backing block. The different layers of the array are bonded together via sintering, lamination, asperity contact, or any other chemical or mechanical structure or technique used to hold the layers together.

Additionally, integrated circuit ("IC") multiplexers, extended flexible circuitry, and/or any other electronic hardware may be disposed in the body or lumen of the imaging tube 110 to couple the transducer arrays 201 and 211 to the imaging system 100, such as an ultrasound machine or system. Alternatively, flex circuit conductors or other conductors electrically connect the elements with cables without further electronics in the catheter.

Referring to FIG. 2 and FIG. 3, which shows a front view of the imaging tube 110 of FIG. 2, the transducer arrays 201 and 211 are disposed in the body or lumen of the imaging tube 110, such as an ultrasonic catheter, along the longitudinal axis 231 and are spaced apart and substantially parallel to each other. For example, the arrays are disposed in front and behind one another. The longitudinal axis 231 of the body of the imaging tube 110 passes through the center of the body. The transducer arrays 201 and 211 are disposed in the center of the body of the imaging tube 110. Alternatively, the transducer arrays 201 and 211 may be spaced apart and disposed away from the center of the body. For example, if the transducer arrays have a shorter height in the range direction, they are disposed in the body with an axis, such as an azimuth axis, that is substantially parallel but not the same as the longitudinal axis. Also, the transducer arrays 201 and 211 may be disposed on different portions of the inner circumference of the body of the imaging tube 110. Therefore, the transducer array 201 may have an azimuth axis that is different than the azimuth axis of the transducer array 211, and both the azimuth axes of the transducer arrays 201 and 211 may be substantially parallel with the longitudinal axis 231.

For any arrangement discussed above, the transducer arrays 201 and 211 are at a non-zero angle 300 to each other about the longitudinal axis 231. The non-zero angle 300 may be in the range from about 1 degree to about 180 degrees. For example, the non-zero angle is in the range of about 5 degrees to about 10 degrees.

Figure 4:
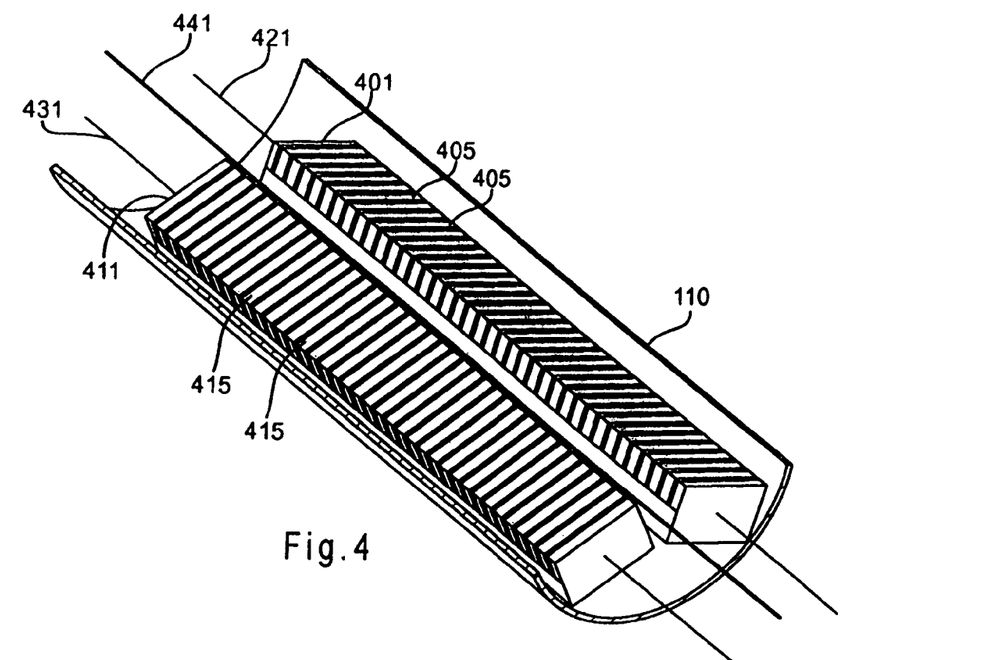
FIG. 4 is a magnified view of an alternate embodiment of the imaging tube of FIG. 1.

Alternatively, instead of arranging the transducer arrays in front or behind each other, the transducer arrays may be arranged side by side or next to each other in the body of the imaging tube 110. FIG. 4 is a magnified view of an alternate embodiment of the imaging tube of FIG. 1. Transducer arrays 401 and 411 are disposed side by side and are substantially parallel to each other in the body of the imaging tube 110. The transducer arrays 401 and 411 are any known or future type of transducer array, such as one dimensional phased transducer arrays similar to the transducer arrays 201 and 211. Also, the transducer arrays 401 and 411 have a plurality of transducer elements 405 and 415, respectively. The transducer elements 405 and 415 may include any number of the features discussed above in regards to the transducer elements 205 and 215.

Figure 5:
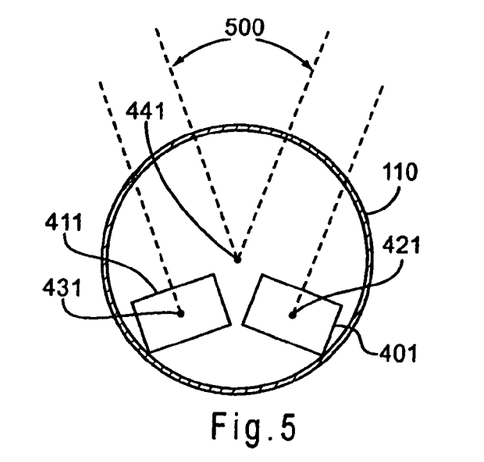
FIG. 5 is a front view of the imaging tube of FIG. 4.

Referring to FIG. 4 and FIG. 5, which shows a front view of the imaging tube 110 of FIG. 4, the transducer array 401 is disposed in the body or lumen of the imaging tube 110, such as an ultrasonic catheter, with an azimuth axis 421, and the transducer array 411 is disposed in the body or lumen with an azimuth axis 431. The axes 421 and 431 are substantially parallel to a longitudinal axis 441. Alternatively, the transducer arrays 401 and 411 may be disposed in the body in such a way that some portions, not the entire arrays, are side by side. Also, the axes 421 and 431 may be positioned at different heights to each other while still being substantially parallel to the longitudinal axis 441.

In any arrangement, the transducer arrays 401 and 411 are at a non-zero angle 500 to each other about the longitudinal axis 441. The non-zero angle 500 is in the range from about 1 degree to about 180 degrees. For example, the non-zero angle is in the range of about 5 degrees to about 10 degrees.

Even though two transducer arrays, such as 201 and 211 or 401 and 411, have been described as being disposed in the imaging tube 110, any number of transducer arrays may be disposed in the imaging tube 110. For example, a third transducer array, similar to the transducer array 201, 211, 401, or 411, is disposed in the body of the imaging tube 110 along the longitudinal axis, such as the axis 231, where the third transducer array is in the center of the body. Alternatively, a third transducer array is disposed in the body or lumen of the imaging tube 110 with an azimuth axis that is substantially parallel but different than the longitudinal axis. The third or any other transducer array may be arranged in any order or combination as described above. Also, any two transducer arrays are at a non-zero angle to each other about the longitudinal axis. For example, the third transducer array and another transducer array, such as the transducer array 211, are at a non-zero angle to each other about the longitudinal axis 231. The non-zero angle is in the range of about 1 degree to about 180 degrees. For example, the non-zero angle is in the range of about 5 degrees to about 15 degrees or may be the same as the non-zero angle 300 or 500.

Figure 6:
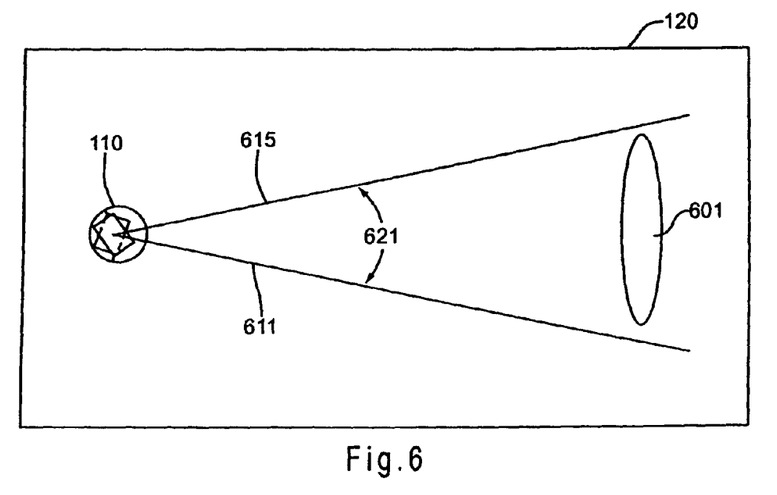
FIG. 6 illustrates the imaging tube of FIG. 1 inserted into a chamber of a heart.

By having transducer arrays at a non-zero angle to each other along the longitudinal axis, doctors or other medical professionals are able to view two separate image planes while maneuvering the image tube 110. FIG. 6 shows the image tube 110, such as an ultrasonic catheter, inserted into a chamber of a heart. For example, the image tube 110, which may utilize any one of the various combinations of transducer arrays described above, is inserted into the patient 120 through a vein. The portion of the image tube 110 encompassing the transducer arrays is positioned in the right atrium of a heart of the patient 120 to view an ostium 601 of a pulmonary vein. The distance between the imaging tube 110 and the ostium 601 is about 7 cm. The diameter of the ostium 601 is about 1 cm, and, therefore, there is about 8 degrees between the center of the imaging tube 110 and the outer circumference of the ostium 601. At least two transducer arrays within the imaging tube 110 are at a non-zero angle 621, such as about 10 degrees, to each other along the longitudinal axis of the body of the imaging tube 110. Acoustic energy 611 emanating from one of the transducer arrays allows for one to view a portion of the ostium 601, and acoustic energy 615 emanating from another transducer array allows for one to view another portion of the ostium 601. As the acoustic energies 611 and 615 travel toward the ostium 601, they become wider or thicker. Their spread of elevation is about 6 degrees. Therefore, if the non-zero angle is too small, resulting images may be blurred due to the spread of elevation.

Any number of 2D images may be viewed based on the number of transducer arrays in the imaging tube 110. The image data for all the 2D images is acquired substantially simultaneously. Therefore, the doctor or medical professional can view a plurality of images in substantially real time, allowing for a 4D like experience. Alternatively, a doctor or medical professional may rotate the imaging tube, via the handle, steering mechanism, or other method, to collect a plurality of image data. Also, the image data of the 2D images may be used to generate a 3D image in substantially real time or at a later time.

Figure 7:
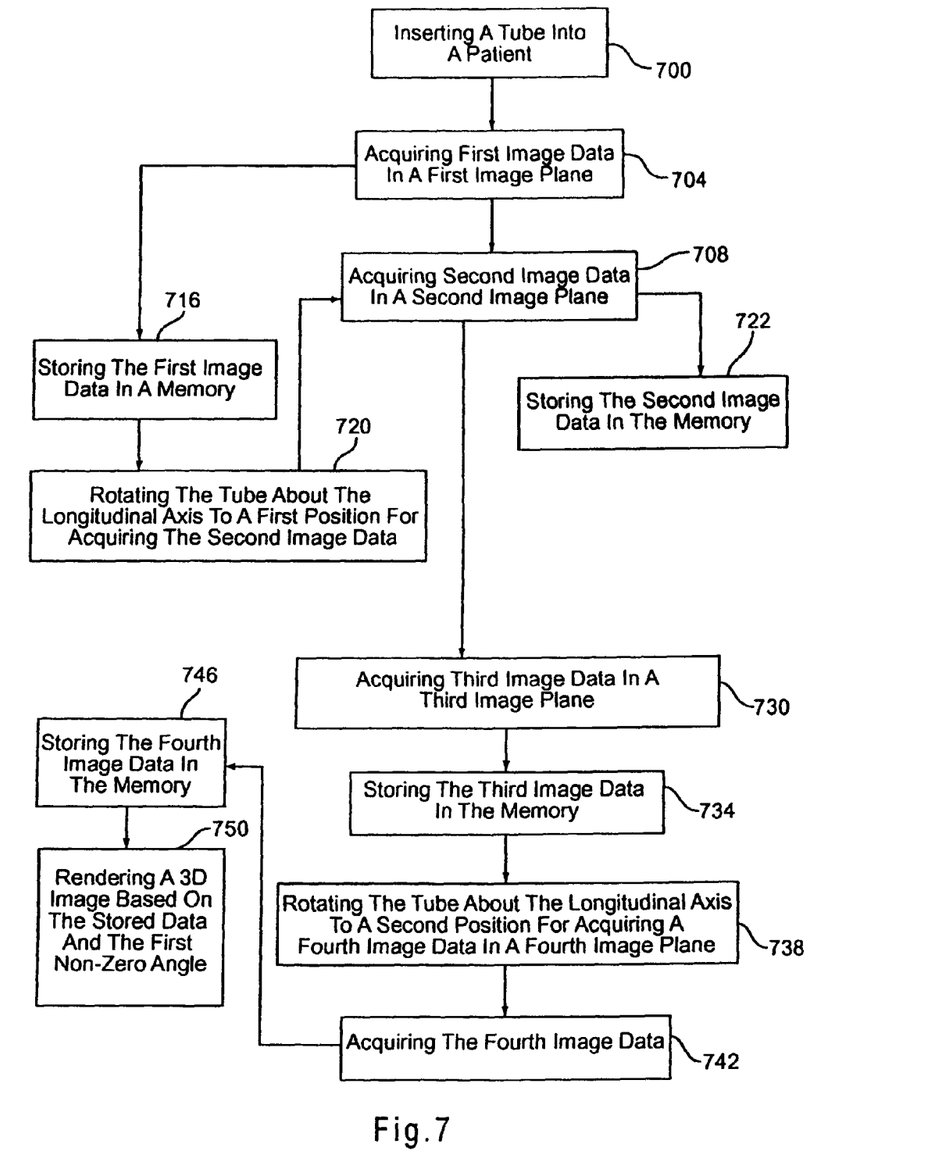
FIG. 7 is a flowchart illustrating examples of methods of imaging.

FIG. 7 is a flowchart illustrating examples of methods of imaging. In act 700, an imaging tube or catheter, such as the imaging tube 110, is inserted into a patient, such as the patient 120. Any known or future methods of inserting the imaging tube or catheter may be utilized. For example, an incision is made in the patient 120, such as in the arm or the leg, and the imaging tube 110 is inserted into the incision by a doctor, medical professional, and/or machine. Alternatively, a needle or puncturing device may be inserted into the patient 120, and the imaging tube 110 follows the puncturing device. Or, the imaging tube is inserted into any orifice or opening of the patient 120. Any known or future lubricant or mechanical, electrical, and/or imaging guide may be used in assisting with inserting the imaging tube 110 into the patient 120.

After the imaging tube is inserted into the patient, the arrays are positioned at a location to acquire images, such as a chamber in the heart. In act 704, image data is acquired in an image plane (first image plane) that is aligned with one of the transducer arrays (first transducer array), such as the transducer array 201, 211, 401, or 411, of the imaging tube 110. The image plane is generally perpendicular to the face of the array 201, 211, 401, or 411. Acoustic energy is transmitted along one or more scan lines within the image plane. Lines 611 and 615 show the direction of the acoustic energy emanating from one of the transducer arrays. Based on acoustic energy echoing back to the transducer array along the same direction, image data in the image plane is acquired. For example, a beamformer is electrically connected with the transducer array and accumulates data from the array. The array 201, 211, 401, or 411 is used to electronically scan the image plane, such as sequential transmission and reception events along scan lines distributed in a linear, Vector®, or sector format.

In act 708, image data is acquired in another image plane (second image plane) that is aligned with another transducer array (second transducer array). Acquiring this image data is similar to acquiring the image data in act 704. Because the transducer arrays are at a non-zero angle to each other, the image planes diverge from each other at that non-zero angle, and the longitudinal axis of the imaging tube 110 is within the image planes outside of the scanned region.

Any number of scans for acquiring image data in any number of image planes is acquired. The acquiring of the image data occurs substantially simultaneously. Alternatively, image data is acquired at different times for each transducer array, or a combination of simultaneous and variant acquisitions occurs for any number of transducer arrays. Spatial, frequency, or other coding may be used to avoid artifacts from acoustic energy for one plane in the scanning of the other plane. Alternatively, sufficient distance or time between scans sufficiently avoids artifacts.

After or during accumulation of image data, a 2D image for each image plane is generated on a display for viewing, such as the display 106 (referring to FIG. 1). For example, image data is directly processed (e.g., by the processor 102) to form a substantially real time image on the display 106. A doctor or medical professional may view the multiple images on a split screen or may flip back and forth between views.

Also, the image data may be stored in a memory, such as the memory 104, as image frames. The image frames may be time marked so that they can be associated with one another appropriately. The time marking is based on real-time clock information or frame number information. The images frames may be stored in storage arrays within the memory 104. Therefore, 2D images may be generated for viewing at any time, even after the imaging tube 110 is removed from the patient.

Furthermore, the imaging tube 110 may be used for an alternate method of imaging. For example, after acquiring image data in the first image plane by the first transducer array, as in act 704, that image data is stored in the memory 104, as in act 716. Any method of storage discussed above may be used.

In act 720, the imaging tube 110 is rotated about its longitudinal axis, such as the longitudinal axis 231, to a position for acquiring additional image data, via another transducer array (such as the second transducer array), in an image plane that is positioned in substantially the same location as the previous image plane. For example, referring to FIG. 6, assuming the imaging tube 110 has already acquired image data of a bottom portion of the ostium 601 via the first transducer array, the image tube 110 is rotated so that the second transducer array can acquire similar image data of the bottom portion of the ostium 601. The degree of rotation is substantially the same as the non-zero angle 621. After and/or during rotation of the imaging tube 110, the second image data corresponding to the second transducer array is acquired, as in act 708.

The image data of the first transducer array may be correlated with the image data of the second transducer array by human estimation or computer/mathematical techniques. For example, a 2D image based on the first image data is displayed, and a 2D image corresponding to the second transducer array is displayed, at substantially real time or a different time during and/or after the rotation of the imaging tube 110. The doctor or medical professional can visually match the images to see if they are substantially similar. A button or input device, which may be part of the control panel 108, may be used to lock on to a specific image data. Alternatively, the first image data can be compared to the present image data during and/or after rotation of the imaging tube 110 by the imaging system 100. The sum of absolute differences technique, cross-correlation, or other correlation can correlate between image frames of the stored data and the present image data. An audio/visual or mechanical indicator can alert the doctor or medical professional as to when the most or sufficiently similar image data has been acquired, and the doctor or medical professional can use the button or input device to lock on to the image data. Alternatively, the imaging system may automatically lock on to the most similar image data.

Changes in position of internal anatomy based on a heart, breathing, or other physiological cycle may be corrected for as well. For example, the imaging system 100 generates a physiological cycle waveform and displays the waveform for assisting a doctor or medical professional when using the imaging tube 110. Alternatively, the imaging system 100 uses the cycle or a portion thereof for triggering purposes when acquiring the image data.

In act 722, the second image data is stored in the memory 104. The storage of the image data occurs when, before, or after the image data is manually or automatically locked on to. Any method of storage discussed above may be used. Alternatively, a plurality of image data is stored periodically or continuously during the rotation of the imaging tube 110.

The imaging tube 110 is rotated more than once to acquire and store more image data for generating a 3D image. For example, after acquiring the second image data via the second transducer array, as in act 708, a third image data is acquired in a third image plane, as in act 730, that is aligned with the first transducer array. Because the imaging tube 110 was rotated, the first transducer array is in a new position that is aligned with the third image plane. In act 734, the third image data is stored in the memory 104. In act 738, the imaging tube 110 is rotated once again to a position for acquiring fourth image data, via the second transducer array, in a fourth image plane that is positioned in substantially the same location as the third image plane. After and/or during rotation of the imaging tube 110, the fourth image data corresponding to the second transducer array is acquired, as in act 742. In act 746, the fourth image data is stored in the memory 104. The stored image data is used for any number of analyses and/or image construction techniques. Any known or future image construction technique may be utilized. For example, volume rendering (including voxel arrangement, coordinate transformation, ray casting, and lighting calculations), surface rendering, image mesh techniques, and/or any other mathematical or digital signal processing method for generating 3D images is used. For example, in act 750, a 3D image is rendered based on the stored data and the non-zero angle between the transducer arrays.

Alternatively, instead of acquiring more image data via additional rotation, extrapolation or interpolation techniques may be utilized. Also, the use of more than two transducer arrays at non-zero angles to each other in the imaging tube 110 allows for more image data acquisition with less or no rotation. Image data may be acquired throughout rotation. The amount of rotation for each scan plane is assumed based on the time between the first array imaging one plane and the second array imaging the same plane.

Any of the above mentioned techniques may be combined to assist in generating an image, such as a 2D, 3D, or 4D image. Any of the features or structural arrangements in regards to the imaging tube 110 and the transducer arrays disposed in the imaging tube 110 discussed above may be arranged into method steps for manufacturing the imaging tube. Also, the features and methods discussed above may be mixed and matched to create a variety of imaging tubes and methods of imaging.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. An ultrasonic imaging tube comprising:
    a tube body having a longitudinal axis and a circumference;
    a first transducer array for imaging disposed in the body with separate elements of the first transducer array spaced along the longitudinal axis; and
    a second transducer array for imaging disposed in the body with separate elements of the second transducer array spaced along the longitudinal axis, the first transducer array substantially parallel with the second transducer array due to the spacing of the separate elements of the first and second transducer arrays and a number of the elements of both the first and second transducer arrays spaced along the longitudinal axis of the tube body, wherein the first transducer array and the second transducer array have faces with corresponding imaging planes that are at a first non-zero angle to each other about the longitudinal axis, the non-zero angle being in a plane orthogonal to the longitudinal axis such that a first emitting face of the first transducer array and a second emitting face of the second transducer array are at different angles in the plane and around the longitudinal axis, the non-zero angle being a difference between the different angles.

2. The ultrasonic imaging tube of claim 1, wherein the first non-zero angle is in the range of about 5 degrees to about 15 degrees.

3. The ultrasonic imaging tube of claim 1, wherein each of the first and second transducer arrays comprise a one dimensional linear phased array.

4. The ultrasonic imaging tube of claim 3, wherein each of the first and second arrays comprise about 64 elements.

5. The ultrasonic imaging tube of claim 1, wherein the elements of each of the first and second transducer arrays comprise at least two layers of transducer material, each of the at least two layers of transducer material operable to convert between electrical and acoustic energies.

6. The ultrasonic imaging of claim 1, wherein each of the first and second transducer arrays comprise a semiconductor substrate supporting a plurality of flexible membranes.

7. The ultrasonic imaging tube of claim 1, further comprising: a third transducer array disposed in the body along the longitudinal axis, wherein the second and third transducer arrays are at a second non-zero angle to each other about the longitudinal axis.

8. The ultrasonic imaging tube of claim 7, wherein the second non-zero angle is the same as the first non-zero angle.

9. The ultrasonic imaging tube of claim 1, wherein the first and second transducer arrays are each substantially parallel with the longitudinal axis and each spaced from a center of the tube body.

10. An ultrasonic imaging catheter comprising:
    a lumen of a catheter operable to connect with an ultrasound machine;
    a first one dimensional linear phased transducer array for imaging disposed in the lumen with a first azimuth axis substantially parallel with a longitudinal axis of the lumen, the first azimuth axis comprising a direction along which elements of the first one dimensional linear phased transducer array are positioned; and
    a second one dimensional linear phased transducer array for imaging disposed in the lumen with a second azimuth axis substantially parallel with the longitudinal axis of the lumen, the second azimuth axis comprising a direction along which elements of the second one dimensional linear phased transducer array are positioned, wherein the first and second one dimensional linear phased transducer arrays have faces with corresponding imaging planes that are at a first non-zero angle to each other about the longitudinal axis and in a plane orthogonal to the longitudinal axis, directions of the first and second arrays, and first and second azimuth axes.

11. The ultrasonic catheter of claim 10, wherein the first non-zero angle is in the range of about 5 degrees to about 15 degrees.

12. The ultrasonic catheter of claim 10, further comprising:
    a third one dimensional linear phased transducer array disposed in the lumen, wherein the second and third one dimensional linear phased transducer arrays are at a second non-zero angle to each other about the longitudinal axis.

13. The ultrasonic catheter of claim 12, wherein the second non-zero angle is in the range of about 5 degrees to about 15 degrees.

14. A method of imaging comprising:
    inserting a tube into a patient, the tube having a longitudinal axis, a circumference in a plane orthogonal to the longitudinal axis, a first transducer array of first elements disposed in the tube, the first elements spaced in a first direction along the longitudinal axis and forming a first planar emitting face, and a second transducer array of second elements disposed in the tube, the second elements spaced in the first direction along the longitudinal axis and forming a second planar emitting face, wherein orthogonal vectors to the first and second planar emitting faces are at a first non-zero angle to each other about the longitudinal axis and in the plane orthogonal to the longitudinal axis, the first transducer array spaced apart from the second transducer array;
    acquiring first image data in a first image plane aligned with the first transducer array; and
    acquiring second image data in a second image plane aligned with the second transducer array, the longitudinal axis being within each of the first and second image planes, the first image plane diverging from the second image plane at the first non-zero angle.

15. The method of claim 14, wherein acquiring the first image data and acquiring the second image data occurs simultaneously.

16. The method of claim 14, wherein acquiring the first image data and acquiring the second image data occurs at different times.

17. The method of claim 16, further comprising:
    storing the first image data in a memory;
    rotating the tube and the first and second transducer arrays about the longitudinal axis to a first position for acquiring the second image data, wherein the second image plane is positioned in a substantially same location as the first image plane was when acquiring the first image data; and storing the second image data in the memory.

18. The method of claim 17, further comprising:

acquiring third image data in a third image plane aligned with the first transducer array;

storing the third image data in the memory;

rotating the tube about the longitudinal axis to a second position for acquiring a fourth image data in a fourth image plane aligned with the second transducer array;

acquiring the fourth image data;

storing the fourth image data in the memory; and rendering a 3D image based on the stored first, second, third, and fourth image data and the first non-zero angle.

* * * * *